(12) United States Patent
Shiojiri et al.

(10) Patent No.: US 7,375,085 B1
(45) Date of Patent: May 20, 2008

(54) MELANOCYTE-STIMULATING HORMONE INHIBITORS

(75) Inventors: Eiji Shiojiri, Kawasaki (JP);
Yoshinobu Takino, Kawasaki (JP);
Hiromi Chujou, Kawasaki (JP);
Kazutami Sakamoto, Kawasaki (JP);
Chiori Ijichi, Kawasaki (JP); Yuzuru Eto, Kawasaki (JP); Keiji Iwasaki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/926,391

(22) PCT Filed: Apr. 25, 2000

(86) PCT No.: PCT/JP00/02687

§ 371 (c)(1),
(2), (4) Date: Jan. 8, 2002

(87) PCT Pub. No.: WO00/64926

PCT Pub. Date: Nov. 2, 2000

(30) Foreign Application Priority Data

Apr. 26, 1999 (JP) .................................. 11-118633

(51) Int. Cl.
*C07K 5/08* (2006.01)
*A61K 38/00* (2006.01)

(52) U.S. Cl. .............................. 514/18; 514/2; 514/19; 530/300; 530/331; 530/333; 530/334; 530/345; 424/9.1

(58) Field of Classification Search .................. 514/18, 514/19, 2; 530/300, 331, 333, 334, 345; 424/9.1
See application file for complete search history.

(56) References Cited

U.S. PATENT DOCUMENTS

| | | | | |
|---|---|---|---|---|
| 2,179,979 A | * | 11/1939 | Isler ........................... | 562/450 |
| 3,619,196 A | * | 11/1971 | Iwama et al. ................ | 430/552 |
| 4,548,926 A | * | 10/1985 | Matsueda et al. ............. | 514/19 |
| 5,861,529 A | * | 1/1999 | Baudoin et al. ................ | 560/9 |
| 6,162,828 A | * | 12/2000 | Fukuda et al. ............... | 514/564 |

FOREIGN PATENT DOCUMENTS

| | | |
|---|---|---|
| EP | 0 093 551 | 11/1983 |
| WO | WO 90/12814 | 11/1990 |
| WO | WO 95/12611 | * 5/1995 |
| WO | WO 98/21229 | 5/1998 |
| WO | WO 00/11022 | 3/2000 |

OTHER PUBLICATIONS

Etzkorn et al., J. Am. Chem. Soc. 1994, 116, 10412-10425.*
Janecka et al., J. Med. Chem. 38, 2922-2924 (1995).*
J. M. Quillan, et al., vol. 92, pp. 2894-2898, "Combinatorial Diffusion Assay Used to Identify Topically Active Melanocyte-Stimulating Hormone Receptor Antagonists", Mar. 1995.
A. Janecka, et al., "Reduced-Size Antogonists of Luteinizing Hormone-Releasing Hormone Active in Vitro", J. Med. Chem., 38, 1995, XP-002125914, first page only.
F.A. Etzkoru, et al., "Cyclic Hexapeptides and Chimeric Peptides as Mimics of Tendamistat", J. Am. Chem. Soc., 116, 1994, XP-002362517, first page only.
C.R. Noe, et al., "Studies on Cyclic Dipeptides, I: Aryl Modifications of Cyclo-(PHE-HIS)#", Monatshefle Fuer Chemi, 127, 1996, XP-009059933, first page only.
M.D. Erion, et al., "Inhibition of Peptidylglycine Alpha-Amidating Monooxygenase by N-Substituted Homocysteine Analogs", J. Med. Chem., 37, 1994, XP-002362519, first page only.
H. Harada, et al., "Synthesis of Human Renin Inhibitory Peptides, Angiotensinogen Transition-State Analogs Containing a Retro-Inverso Amide Bond", Chem. Pharm. Bull., 38 (11), 1990, XP-000919337, first page only.
J.R. Luly, et al., "New Inhibitors of Human Renin That Contain Novel Leu-Val Replacements", Journal of Medicinal Chemistry, American Chemical Society. Washington, US, vol. 30, No. 9, 1987, XP-001053395, first page only.
S. Gerisch, et al., "Enzymatic Peptide Synthesis in Frozen Aqueous Systems: Use of Nalpha-Unprotected Unusual Acyl Donors", Tetrahedron: Asymmetry, vol. 6, No. 12, 1995, XP-004047955, first page only.
M. Akazome, et al., "Enantiomeric Inclusion of Alpha-Hydroxy Esters by (R)-(1-Naphtyl)Glycyl-(R)-Phenylglycine and the Crystal Structures of the Inclusion Cavities", J. Org. Chem., 64, 1999, XP-002362520, first page only.
Y. Inai, et al., "Distance and Orientation Dependence of Electron Transfer and Exciplex Formation of Naphthyl and P-Dimethylanilino Groups Fixed on a Helical Polylpeptide Chain", J. Phys. Chem., 94, 1990, XP-002362521, first page only.
A. Janecka, et al., "Reduced-Size Antagonists of Luteinizing Hormone-Releasing Hormone Active in Vitro", J. Med. Chem., 38, 1995, XP-002125914, pp. 2922-2924.
F.A. Etzkorn, et al., "Cyclic Hexapeptides and Chimeric Peptides as Mimics of Tendamistat", J. Am. Chem. Soc., 116, 1994, XP-002362517, pp. 10412-10425.
C.R. Noe, et al., "Studies on Cyclic Dipeptides, I: Aryl Modifications of Cyclo-(PHE-HIS)#", Monatshefte Fuer Chemi, 127, 1996, XP-009059933, pp. 1081-1097.
M.D. Erion, et al., "Inhibition of Peptidylglycine Alpha-Amidating Monooxygenase by N-Substituted Homocysteine Analogs", J. Med. Chem., 37, 1994, XP-002362519, pp. 4430-4437.

(Continued)

*Primary Examiner*—Chih-Min Kam
(74) *Attorney, Agent, or Firm*—Oblon, Spivak, McClelland, Maier & Neustadt, P.C.

(57) ABSTRACT

In the present specification is disclosed a melanocyte-stimulating hormone inhibitory composition which comprises, as the active ingredient, a di- or tripeptide derivative having a certain naphthyl group or the salts thereof, or a melanocyte-stimulating hormone inhibitory compound having a 50% inhibitory concentration of cAMP production (IC50) of 100 nM or less, which composition can prevent pigmentation, or can prevent, improve or recover from immune abnormality or immunodeficiency, or regulate body weight by appetite control, and also can be used as cosmetics or external preparations for the skin, and in addition, can be produced easily, and are excellent in the stability during storage.

18 Claims, 1 Drawing Sheet

OTHER PUBLICATIONS

H. Harada, et al., "Synthesis of Human Renin Inhibitory Peptides, Angiotensinogen Transition-State Analogs Containing a Retro-Inverso Amide Bond", Chem. Pharm. Bull., 38 (11), 1990, XP-000919337, pp. 3042-3047.

J.R. Luly, et al., "New Inhibitors of Human Renin That Contain Novel Leu-Val Replacements", Journal of Medicinal Chemistry, American Chemical Society. Washington, US, vol. 30, No. 8, 1987, XP-001053395, pp. 1609-1616.

S. Gerisch, et al., "Enzymatic Peptide Synthesis in Frozen Aqueous Systems: Use of Nalpha-Unprotected Unusual Acyl Donors", Tetrahedron: Asymmetry, vol. 6, No. 12, 1995, XP-004047955, pp. 3039-3045.

M. Akazome, et al., "Enantiomeric Inclusion of Alpha-Hydroxy Esters by (R)-(1-Naphtyl)Glycyl-(R)-Phenylglycine and the Crystal Structures of the Inclusion Cavities", J. Org. Chem., 64, 1999, XP-002362520, pp. 2293-2300.

Y. Inai, et al., "Distance and Orientation Dependence of Electron Transfer and Exciplex Formation of Naphthyl and P-Dimethylanilino Groups Fixed on a Helical Polylpeptide Chain", J. Phys. Chem., 94, 1990, XP-002362521, pp. 6237-6243.

Abdel-Malek, Z., et al., "Mitogenic and Melanogenic Stimulation of Normal Human Melanocytes by Melanotropic Peptides," Proc. Natl. Acad. Sci., Cell Biology, vol. 92, Feb. 1995, pp. 1789-1793.

Taylor, A. W., et al., "Alpha-Melanocyte-Stimulating Hormone Suppresses Antigen-Stimulated T Cell Production of Gamma-Interferon," Neuroimmunomodulation 1994, vol. 1, pp. 188-194.

Hiltz, M. E., et al., "α-MSH Peptides Inhibit Acute Inflammation Induced in Mice by rIL-1β, rIL-6, rTNF-α and Endogenous Pyrogen but Not That Caused by $LTB_4$, PAF and rIL-8," Cytokine, vol. 4, No. 4, Jul. 1992, pp. 320-328.

Ludwig, D. S., et al., "Melanin-Concentrating Hormone: A Functional Melanocortin Antagonist in the Hypothalamus," American Physiological Society, 1998, vol. 274, pp. E627-E633.

A. Janecka, et al., "Reduced-Size Antagonists of Luteinizing Hormone-Releasing Hormone Active in Vitro", J. Med. Chem., 38, 1995, XP-002125914, first page only, p. 2922-2924.

F.A. Etzkoru, et al., "Cyclic Hexapeptides and Chimeric Peptides as Mimics of Tendamistat", J. Am. Chem. Soc., 116, 1994, XP-002362517, first page only, p. 10412-10423.

C.R. Noe, et al., "Studies on Cyclic Dipeptides, I: Aryl Modifications of Cyclo-(PHE-HIS)#", Monatshefte Fuer Chemi, 127, 1996, XP-009059933, first page only p. 1081-1097.

M.D. Erion, et al., "Inhibition of Peptidylglycine Alpha-Amidating Monooxygenase by N-Substituted Homocysteine Analogs", J. Med. Chem., 37, 1994, XP-002362519, first page only, p. 4430-4437.

H. Harada, et al., "Synthesis of Human Renin Inhibitory Peptides, Angiotensiogen Transition-State analogs Containing a Retro-Inverso Amide Bond", Chem. Pharm. Bull., 38 (11), 1990, XP-000919337, first page only, p. 3042-3047.

J.R. Luly, et al., "New Inhibitors of Human Renin That Contain Novel Leu-Val Replacements", Journal of Medicinal Chemistry, American Chemical Society. Washington, US, vol. 30, No. 9, 1987, XP-001053395, first page only, p. 1609-1616.

S. Gerisch, et al., "Enzymatic Peptide Synthesis in Frozen Aqueous Systems: Use of Nalpha-Unprotected Unusual Acyl Donors", Tetrehedron: Asymmetry, vol. 6, No. 12, 1995, XP-004047955, first page only, p. 3039-3045.

M. Akazome, et al., "Enantiomeric Inclusion of Alpha-Hydroxy Esters by (R)-(1-Naphtyl)Glycyl-(R)-Phenylglycine and the Crystal Structures of the Inclusion Cavities", J. Org. Chem., 64, 1999, XP-002362520, first page only, p. 2293-2300.

Y. Inai, et al., "Distance and Orientation Dependence of electron Transfer and Exciplex Formation of Naphthyl and P-Dimethylanilino Groups Fixed on a Helical Polylpeptide Chain", J. Phys. Chem., 94, 1990, XP-002362521, first page only, p. 6237-6243.

* cited by examiner

○ D-2-Nal-Arg-Leu-NH$_2$ (50mM)-applied group

● D-Trp-Arg-Leu-NH$_2$ (50mM)-applied group (n = 5, Average value)

ΔL*Value (——○——) =
　　L*Value (D-2-Nal-Arg-Leu-NH$_2$-applied) − L*Value (Ethanol-applied)

ΔL*Value (——●——) =
　　L*Value (D-Trp-Arg-Leu-NH$_2$-applied) − L*Value (Ethanol-applied)

US 7,375,085 B1

MELANOCYTE-STIMULATING HORMONE INHIBITORS

This application is a 371 of PCT/JP00/02687, filed Apr. 25, 2000, which claims the foreign priority of Japan 11/118633, filed Apr. 26, 1999.

TECHNICAL FIELD

The present invention relates to novel peptide derivatives having an inhibitory activity of melanocyte-stimulating hormone, and melanocyte-stimulating hormone inhibitory compositions, as well as to a whitening agent, an immunofunction regulator, an appetite regulator, a cosmetic or a skin preparation for external use, which comprises at least one of the said novel peptide derivatives and the said inhibitory compositions.

BACKGROUND ART

Melanocyte-stimulating hormone is known to participate in the control of the colors of the skin and hair of humans and animals, and to darken the color of the human skin (e.g., Nature (1961) 189, 176-179). It is reported as the main cause of such action that melanocyte-stimulating hormone accelerates the growth of melanocytes and also activates tyrosinase which is an enzyme for the biosynthesis of melanin (Proc. Natl. Acad. Sci. (1995) 92, 1789-1793). On the other hand, it is known that melanocyte-stimulating hormone is produced by skin epidermal cells, and that the production amount is increased largely by the irradiation of ultraviolet rays (ACTH Relat. Rept. (1995) 6, 63-68). It is thought from these facts that melanocyte-stimulating hormone is the main cause of pigmentation after sunburn by ultraviolet rays.

As other actions of melanocyte-stimulating hormone, there are known an inhibitory action of the production of nitrogen monoxide by macrophages and an immunosuppressive action through IL-10 (e.g., Immunology Today (1997) 18, 140-145) and an appetite-controlling action (e.g., Am. J. Physiol. 274 Endocrinol. Metab. 37 (1998) E627-E633).

Accordingly, the suppression of the formation of melanocyte-stimulating hormone or the inhibition of the action thereof can realize the prevention of pigmentation to be caused by ultraviolet rays, the prevention, improvement or recovery of or from immune abnormality or immunodeficiency, or the regulation of body weight by appetite control.

Hitherto, there have been known as melanocyte-stimulating hormone inhibitors, His-D-Arg-Ala-Trp-D-Phe-Lys-NH$_2$ (Peptides (1994) 15, 627-632), D-Trp-Arg-Leu-NH$_2$ (Proc. Natl. Acad. Sci. (1995) 92, 2894-2898), and the like. However, these inhibitors all contain tryptophan which is an unstable amino acid, and therefore there is a problem that the stability during storage is inferior. Moreover, these inhibitors are known to decolor the skin of reptiles and the pigment cells of amphibians, but it has not been clarified whether they have the action of suppressing the formation of melanin and the activation of tyrosinase by melanocyte-stimulating hormone, which cause the pigmentation of the human skin.

Moreover, as other melanocyte-stimulating hormone inhibitors, it is known that an agcuti protein and fragment peptides thereof have a pigmentation inhibitory action (WO 97/00892), but there are problems that the production thereof is not facile and that the stability during storage thereof is inferior.

Furthermore, there are problems that some melanocyte-stimulating hormone inhibitors which even show effects of decoloring pigment cells, and the like, upon the evaluation with cells, exhibit only weak effects, and that the expression of the effects takes some period of time even though they exhibit effects such as the prevention of pigmentation, the prevention, improvement or recovery of or from immune abnormality or immunodeficiency, the regulation of body weight by appetite control, or the like, in the case of their actual application to living body.

DISCLOSURE OF THE INVENTION

Under the circumstance of the background art as has been described above, a first object of the present invention is to provide novel peptide derivatives, which can inhibit the action of melanocyte-stimulating hormone, whereby the pigmentation by ultraviolet rays can be prevented, can prevent, improve or recover from immune abnormality or immunodeficiency, or regulate body weight by appetite control, and also can be used as cosmetics or external preparations for the skin, and in addition, can be produced easily, and are excellent in the stability during storage.

Moreover, a second object of the present invention is to provide a melanocyte-stimulating hormone inhibitory composition which has a remarkably excellent inhibitory effect of pigmentation, are effective for the prevention, improvement or recovery of or from immune abnormality or immunodeficiency, or can regulate body weight by appetite control, and also can be used as cosmetics or external preparations for the skin, when actually applied to the living body.

As a result of the extensive studies for attaining the above first object, the present inventors have found that the above first object can be attained with novel peptide derivatives represented by the following general formula (1) or salts thereof, and accomplished the present invention based on such findings.

Accordingly, the present invention relates to di- or tripeptide derivatives having a naphthyl group and represented by the following general formula (1) or salts thereof.

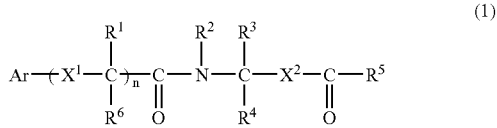

(1)

(wherein Ar represents a naphthyl group which may have substituent(s), $R^1$, $R^2$ and $R^3$ represent each independently a hydrogen atom or a straight-chain or branched-chain alkyl group having 1 to 6 carbon atoms which may have substituent(s), $R^4$ represents a hydrogen atom, an amino acid side chain, an amino group, an amidino group, a guanidinyl group, a straight-chain or branched-chain aminoalkyl group having 1 to 6 carbon atoms, a straight-chain or branched-chain amidinoalkyl group having 1 to 6 carbon atoms, a straight-chain or branched-chain guanidinoalkyl group having 1 to 6 carbon atoms, or an amidinoaryl group having 6 to 12 carbon atoms, all of which may have substituent(s), $X^1$ is actually absent (i.e., nothing) or an alkylene group having 1 or 6 carbon atoms, an aminoalkylene group having 1 to 6 carbon atoms which may have as a substituent a straight-chain or branched-chain alkyl group having 1 to 6 carbon atoms, or a straight-chain or branched-chain oxyalkylene group having 1 to 6 carbon atoms, $X^2$ is actually absent or a straight-chain or branched-chain alkylene group having 1 to 6 carbon atoms, $R^6$ represents a hydrogen atom or —NHY, wherein Y represents a hydrogen atom, an acyl group having 2 to 22 carbon atoms, an alkyl group having 1 to 22 carbon atoms, a hydroxyalkyl group having 1 to 22 carbon atoms, or a 3-alkoxy-2-hydroxypropyl group having an alkoxyl group having 1 to 22 carbon atoms, n represents an integer of 0 or 1, and $R^5$ represents a group represented by the following general formula (2),

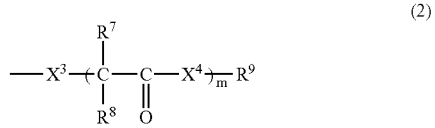

(2)

wherein $X^3$ represents —O— or —$NR^{10}$—, $X^4$ represents —O— or —$NR^{11}$—, $R^7$ represents a hydrogen atom, an amino acid side chain or a straight-chain or branched-chain alkyl group having 1 to 6 carbon atoms, $R^8$, $R^{10}$, and $R^{11}$ represent each independently a hydrogen atom or a straight-chain or branched-chain alkyl group having 1 to 6 carbon atoms, $R^9$ represents a hydrogen atom, an acyl group having 2 to 22 carbon atoms, an alkyl group having 1 to 22 carbon atoms, a hydroxyalkyl group having 1 to 22 carbon atoms, or a 3-alkoxy-2-hydroxypropyl group whose alkoxyl group is an alkoxy group having 1 to 22 carbon atoms, and m represents an integer of 0 or 1.).

It is to be noted that the peptide derivatives represented by the above general formula (1) are novel compounds which have not been described in the literature.

Moreover, as a result of extensive studies for attaining the above second object, i.e., finding a compound exhibiting remarkable effects such as pigmentation inhibitor and the like, in the case of actual application to living body, the present inventors have found that compounds having an inhibitory activity of melanocyte-stimulating hormone and having a certain cAMP production inhibitory action can attain the above second object, and accomplished the present invention. By the way, such compounds are not limited to the peptide derivatives represented by the above general formula (1) or salts thereof.

Accordingly, the present invention relates to a melanocyte-stimulating hormone inhibitory composition which comprises, as the active ingredient, a compound having an inhibitory activity of melanocyte-stimulating hormone, the said compound showing a 50% inhibitory concentration of cAMP (cyclic adensine 3',5'-monophosphate) production (IC50) of 100 nM or less.

Moreover, the present invention relates to a melanocyte-stimulating hormone inhibitory composition which comprises, as the active ingredient, at least one selected from the peptide derivatives represented by the above general formula (1) or salts thereof.

Furthermore, the present invention relates to a whitening agent, an immunofunction regulator, an appetite regulator, a cosmetic or a skin preparation for external use, which comprises, as the active ingredient, at least one of such melanocyte-stimulating hormone inhibitory compositions or the compounds having an inhibitory activity of melanocyte-stimulating hormone, the said compounds showing a 50% inhibitory concentration of cAMP production (IC50) of 100 nM or less.

In the following will be described the present invention in greater detail.

In the peptide derivatives of the present invention represented by the general formula (1) and salts thereof, $R^6$ is defined as described above, and specific examples of Y in the case where $R^6$ is NHY, include a hydrogen atom, and an acetyl group, popionyl group, isopropionyl group, n-butyroyl group, isobutyroyl group, sec-butyroyl group, tert-butyroyl group, n-amyloyl group, sec-amloyl group, tert-amyloryl group, isoamyloyl group, n-hexyloyl group, cyclohexyloyl group, n-heptanoyl group, n-octanoyl group, 2-ethylhexyloyl group, nonyoyl group, isononyoyl group, decanoyl group, isodecanoyl group, undecanoyl group, lauroyl group, tridecanoyl group, isotridecanoyl group, myristoyl group, palmitoyl group, isopalmitoyl group, stearoyl group, isostearoyl group, oleoyl group, docosanoyl group, methyl group, ethyl group, propyl group, isopropyl group, n-butyl group, isobutyl group, sec-butyl group, tert-butyl group, n-amyl group, sec-amyl group, tert-amyl group, isoamyl group, n-hexyl group, cyclohexyl group, n-heptyl group, n-octyl group, 2-ethylhexyl group, nonyl group, isononyl group, decyl group, isodecyl group, undecyl group, lauryl group, tridecyl group, isotridecyl group, myristyl group, cetyl group, isocetyl group, stearyl group, isostearyl group, oleyl group, behenyl group, 2-hydroxyethyl group, 2-hydroxypropyl group, 2-hydroxyisopropyl group, 2-hydroxy-n-butyl group, 2-hydroxyisobutyl group, 2-hydroxy-sec-butyl group, 2-hydroxy-tert-butyl group, 2-hydroxy-n-amyl group, 2-hydroxy-sec-amyl group, 2-hydroxy-tert-amyl group, 2-hydroxyisoamyl group, 2-hydroxy-n-hexyl group, 2-hydroxycyclohexyl group, 2-hydroxy-n-heptyl group, 2-hydroxy-n-octyl group, 2-hydroxy-2-ethylhexyl group, 2-hydroxynonyl group, 2-hydroxyisononyl group, 2-hydroxydecyl group, 2-hydroxyisodecyl group, 2-hydroxyundecyl group, 2-hydroxylauryl group, 2-hydroxytridecyl group, 2-hydroxyisotridecyl group, 2-hydroxymyristyl group, 2-hydrocycetyl group, 2-hydroxyisocetyl group, 2-hydroxystearyl group, 2-hydroxyisostearyl group, 2-hydroxyoleyl group, 2-hydroxybehenyl group, 3-methoxy-2-hydroxypropyl group, 3-ethoxy-2-hydroxypropyl group, 3-propoxy-2-hydroxypropyl group, 3-isopropoxy-2-hydroxypropyl group, 3-n-butoxy-2-hydroxypropyl group, 3-isobutoxy-2-hydroxypropyl group, 3-sec-butoxy-2-hydroxypropyl group, 3-tert-butoxy-2-hydroxypropyl group, 3-n-amyloxy-2-hydroxypropyl group, 3-sec-amyloxy-2-hydroxypropyl group, 3-tert-amyloxy-2-hydroxypropyl group, 3-isoamyloxy-2-hydroxypropyl group, 3-n-hexyloxy-2-hydroxypropyl group, 3-cyclohexyloxy-2-hydroxypropyl group, 3-n-heptyloxy-2-hydroxypropyl group, 3-n-octyloxy-2-hydroxypropyl group, 3-(2-ethylhexyl)oxy-2-hydroxypropyl group, 3-nonyloxy-2-hydroxypropyl group, 3-isononyloxy-2-hydroxypropyl group, 3-decyloxy-2-hydroxypropyl group, 3-isodecyloxy-2-hydroxypropyl group, 3-undecyloxy-2-hydroxypropyl group, 3-lauryloxy-2-hydroxypropyl group, 3-tridecyloxy-2-hydroxypropyl group, 3-isotridecyloxy-2-hydroxypropyl group, 3-myristyloxy-2-hydroxypropyl group, 3-cetyloxy-2-hydroxypropyl group, 3-isocetyloxy-2-hydroxypropyl group, 3-stearyloxy-2-hydroxypropyl group, 3-isostearyloxy-2-hydroxypropyl group, 3-oleyloxy-2-hydroxypropyl group, 3-behenyloxy-2-hydroxypropyl group, and the like.

The position where Ar and $X^1$, both defined as above, are bonded to each other, is not particularly limited and any position may be optionally selected. And, the hydrogen atom(s) bonded to the aromatic ring of these groups may be replaced by one or more of halogen atoms, alkyl groups having 1 to 6 carbon atoms, hydroxyl groups, hydroxyalkyl groups having 1 to 6 carbon atoms, nitro groups, alkoxyl groups having 1 to 6 carbon atoms, or carboxyl groups, or sulfonic acid groups. In the case that the hydrogen atoms are replaced by two or more groups, the two or more substituents may be the same or different.

As the mother skeleton of Ar, there may be mentioned 1-naphthyl group or 2-naphthyl group.

As specific examples of $R^4$ defined as above, there may be mentioned amino acid side chains (by amino acid side chain being meant a residue resulting from the removal of $C(COOH)NH_2$ from an amino acid) derivable from acidic amino acids such as glutamic acid, aspartic acid, cysteic acid, homocysteic acid, and the like, neutral amino acids such as alanine, β-alanine, 2-aminobutyric acid, valine, norvaline, leucine, norleucine, isoleucine, phenylalanine, phenylglycine, threonine, serine, homoserine, tyrosine, dopa, cysteine, methionine, glutamine, asparagine, and the like, and basic amino acids such as lysine, homolysine, ornithine, arginine, homoarginine, histidine, and the like; or a hydrogen atom. Among them, more preferred are the side chains derivable from basic amino acids. Other than the side chains derivable from the amino acids, there may be mentioned amidinoethyl, amidinopropyl, amidinobutyl, amidinopentyl, amidinohexyl, amidinophenyl, and the like, having an amidino group.

Specific examples of $R^7$ in the general formula (2) defined as above include amino acid side chains derivable from acidic amino acids such as glutamic acid, aspartic acid, cysteic acid, homocysteic acid, and the like, neutral amino acids such as alanine, β-alanine, 2-aminobutyric acid, valine, norvaline, leucine, norleucine, isoleucine, phenylalanine, phenylglycine, tryptophan, threonine, serine, homoserine, tyrosine, dopa, cysteine, methionine, glutamine, asparagine, and the like, and basic amino acids such as lysine, homolysine, ornithine, arginine, homoarginine, histidine and the like; or a hydrogen atom. Among them, more preferred are the amino acid side chains derivable from neutral amino acids having a hydrophobic side chain.

Specific examples of $R^9$ defined as above include a hydrogen atom, a methyl group, ethyl group, propyl group, isopropyl group, n-butyl group, isobutyl group, sec-butyl group, tert-butyl group, n-amyl group, sec-amyl group, tert-amyl group, isoamyl group, n-hexyl group, cyclohexyl group, n-heptyl group, n-octyl group, 2-ethylhexyl group, nonyl group, isononyl group, decyl group, isodecyl group, undecyl group, lauryl group, tridecyl group, isotridecyl group, myristyl group, cetyl group, isocetyl group, stearyl group, isostearyl group, oleyl group, vehenyl group, 2-hydroxyethyl group, 2-hydroxypropyl group, 2-hydroxyisopropyl group, 2-hydroxy-n-butyl group, 2-hydroxyisobutyl group, 2-hydroxy-sec-butyl group, 2-hydroxy-tert-butyl group, 2-hydroxy-n-amyl group, 2-hydroxy-sec-amyl group, 2-hydroxy-tert-amyl group, 2-hydroxyisoamyl group, 2-hydroxy-n-hexyl group, 2-hydroxycyclohexyl group, 2-hydroxy-n-heptyl group, 2-hydroxy-n-octyl group, 2-hydroxy-2-ethylhexyl group, 2-hydroxynonyl group, 2-hydroxyisononyl group, 2-hydroxydecyl group, 2-hydroxyisodecyl group, 2-hydroxyundecyl group, 2-hydroxylauryl group, 2-hydroxytridecyl group, 2-hydroxyisotridecyl group, 2-hydroxymyristyl group, 2-hydroxycetyl group, 2-hydroxyisocetyl group, 2-hydroxystearyl group, 2-hydroxyisostearyl group, 2-hydroxyoleyl group, 2-hydroxybehenyl group, 3-methoxy-2-hydroxypropyl group, 3-ethoxy-2-hydroxypropyl group, 3-propoxy-2-hydroxypropyl group, 3-isopropoxy-2-hydroxypropyl group, 3-n-butoxy-2-hydroxypropyl group, 3-isobutoxy-2-hydroxypropyl group, 3-sec-butoxy-2-hydroxypropyl group, 3-tert-butoxy-2-hydroxypropyl group, 3-n-amyloxy-2-hydroxypropyl group, 3-sec-amyloxy-2-hydroxypropyl group, 3-tert-amyloxy-2-hydroxypropyl group, 3-isoamyloxy-2-hydroxypropyl group, 3-n-hexyloxy-2-hydroxypropyl group, 3-cyclohexyloxy-2-hydroxypropyl group, 3-n-heptyloxy-2-hydroxypropyl group, 3-n-octyloxy-2-hydroxypropyl group, 3-(2-ethylhexyl)oxy-2-hydroxypropyl group, 3-nonyloxy-2-hydroxypropyl group, 3-isononyloxy-2-hydroxypropyl group, 3-decyloxy-2-hydroxypropyl group, 3-isodecyloxy-2-hydroxypropyl group, 3-undecyloxy-2-hydroxypropyl group, 3-lauryloxy-2-hydroxypropyl group, 3-tridecyloxy-2-hydroxypropyl group, 3-isotridecyloxy-2-hydroxypropyl group, 3-myristyloxy-2-hydroxypropyl group, 3-cetyloxy-2-hydroxypropyl group, 3-isocetyloxy-2-hydroxypropyl group, 3-stearyloxy-2-hydroxypropyl group, 3-isostearyloxy-2-hydroxypropyl group, 3-oleyloxy-2-hydroxypropyl group, 3-behenyloxy-2-hydroxypropyl group, and the like.

The residue of each amino acid of the peptide derivatives represented by the above general formula (1) may be either optically active one or racemic one.

Specific examples of the salts of the compounds represented by the above general formula (1) include physiologically acceptable salts, for example, inorganic salts, e.g., those of alkali metals such as sodium, potassium and the like, those of alkaline earth metals such as magnesium, calcium and the like, ammonium salts, and the like; organic amine salts, e.g., those of monoethanolamine, diethanolamine, triethanolamine, 2-amino-2-methyl-1-propanol, 2-amino-2-methyl-1,3-propanediol, lysine, ornithine, arginine and the like; halogen salts, e.g., those of chlorine, bromine, iodine and the like; inorganic acid salts, e.g., hydrochloride, sulfate, carbonate, phosphate and the like; organic acid salts, e.g., acetates, trifluoroacetates, tartrates, citrates, p-toluenesulfonates, glycolates, malates, lactates, fatty acid salts, acidic amino acid salts and pyroglutamates; and the like. Two or more of these salts may be used in combination.

The peptide derivatives of the present invention represented by the above general formula (1) can be synthesized, for example, as follows. First, a protected basic amino acid and a neutral amino acid whose carboxyl group has been amidated are condensed with a water-soluble carbodiimide in methylene chloride, and successive treatment such as acid treatment affords a protected dipeptide wherein only the protective group on the main chain has been removed. Next, the protected dipeptide and an N-terminal protected amino acid derivative having an aryl group such as naphthylmethyl group or the like on the side chain are condensed with a water-soluble carbodiimide in methylene chloride, and the protective group of the resulting protected tripeptide is removed by, for example, reduction in the presence of palladium-carbon catalyst, whereby an aimed-at peptide derivative is obtained. Further, various derivatives wherein the N-terminal amino group is acylated, alkylated, hydroxyalkylated or 3-alkoxy-2-hydroxypropylated, can be obtained by, for example, reacting a protected tripeptide whose N-terminal is only deprotected, with an acid anhydride, an acid chloride, an alkyl halide, an epoxyalkane or an alkyl glycidyl ether, followed by reductive deprotection in the presence of palladium-carbon catalyst, and the like.

Moreover, a tripeptide whose C-terminal is a carboxyl group can be obtained by catalytic reduction of a tripeptide similarly obtained using a neutral amino acid whose carboxyl group is protected with a benzyl group instead of the neutral amino acid whose carboxyl group is amidated. Furthermore, various derivatives can be obtained by subjecting an N-terminal amino group to acylation, alkylation, hydroxyalkylation or 3-alkoxy-2-hydroxypropylation in a step precedent to the step of removing the benzyl group which is a protective group of the basic amino acid side chain or a protective group of the carboxyl group, and successive catalytic reduction. Furthermore, dehydrative condensation of the peptide derivatives with an alcohol in the presence of an acid catalyst affords various C-terminal carboxylic ester derivatives.

In addition, a derivative whose C-terminal carboxyl group is esterified or amidated can be obtained by dehydrative condensation of a tripeptide whose C-terminal is a carboxyl group and whose amino group on the main chain and basic amino acid side chain have been protected, with an alkylamine or addition reaction of the tripeptide with an epoxyalkane or an alkyl glycidyl ether, followed by similar successive catalytic reduction.

The 50% inhibitory concentration of cAMP production (IC50) according to the present invention regarding the compounds having a melanocyte-stimulating hormone (MSH) inhibitory activity is measured and defined as follows.

Namely, B16 melanoma cells are inoculated on a 12-well plate in such way that $1\times10^4$ cells are inoculated into 1 well, and cultured at 37° C. for 48 hours in the presence of 5% $CO_2$. After the culturing, the wells are washed with 1 ml of a serum-free medium (serum-free D-MEM medium) per 1 well. Then, a serum-free medium containing 1 mM 3-isobutyl-1-methylxanthine, 10 nM melanocyte-stimulating hormone and a compound to be tested at a different concentration is added in an amount of 1 ml per 1 well, followed by incubation at 37° C. for 5 minutes. After the incubation, the medium is completely removed from the plate, 1 ml of ice-cooled 2.5% perchloric acid is exactly added thereto, and then the whole is incubated for 30 minutes under ice-cooling to extract cAMP from within the cells. After the incubation, the extract solution is neutralized by adding 4.2M potassium hydroxide solution in an amount of 90 ml per 1 well.

The neutralized extract solution is centrifuged at 4° C. at 12,000 rpm for 10 minutes, and the amount of cAMP in the supernatant is quantitatively determined using "Biotrak cAMP EIA System" (manufactured by Amersham Pharmacia Biotech), as follows. By the way, all the operations are carried out at 5° C. or lower. First, cAMP authentic samples are prepared so as to be 0 to 3200 fM, and each sample is placed in an amount of 100 µl in a 96-well plate. Then, 200 µl of 0.05M acetate buffer (pH 5.8, containing 0.02% serum and 0.01% antiseptic agent) is placed in an NSB well (Non-specific Binding Well) and 100 µl in a blank well. In a sample well is placed 100 µl of a sample to be evaluated. In each of all the wells except for the blank well and the NSB well is added 100 µl of antiserum. The 96-well plate is capped, slowly shaken, and incubated at 3 to 5° C. for 2 hours. After the incubation, 50 µl of cAMP peroxidase is added to each of all the wells except for the blank well. The plate is capped and incubated at 3 to 5° C. for 1 hour. After the incubation, each of all the wells is washed four times with 400 µl in total of 0.01M phosphate buffer (pH 7.5, containing 0.05% "Tween 20"). The liquid remaining in the wells is removed by placing the plate in such manner that the opening parts of the wells face downward, and patting the plate on a paper.

To each of all the wells is added 150 µl of an enzyme substrate, and the plate is shaken at 15 to 30° C. for 1 hour. After the shaking, 100 µl of 1 M sulfuric acid is added to each well, and absorbance at 450 nm is measured. A calibration curve is prepared from the absorbance of the cAMP authentic samples and the amount of cAMP of each sample is determined.

The 50% inhibitory concentration of cAMP production (IC50) is defined by the value in terms of nM unit, of a 50% inhibitory concentration obtained by the above procedures, of a test compound against cAMP production with 10 nM melanocyte-stimulating hormone.

Among the melanocyte-stimulating hormone inhibiting compounds of the present invention exhibiting a 50% inhibitory concentration of cAMP production (IC50) of 100 nM or less, particularly preferred are those inhibiting pigmentation by ultraviolet rays for employing as a whitening agent.

Moreover, the melanocyte-stimulating hormone inhibiting compounds of the present invention exhibiting a 50% inhibitory concentration of cAMP production (IC50) of 100 nM or less have preferably a molecular weight of 800 or less, more preferably 200 to 600, from the view-point of percutaneous absorbability, intestinal absorbability, solubility, easiness of production, and the like.

The melanocyte-stimulating hormone inhibitory composition, whitening agent, immunofunction controlling agent, appetite controlling agent, cosmetic and external preparation for the skin of the present invention, which comprise, as the active ingredient, a peptide derivative represented by the above general formula (1) or a salt thereof, may be prepared optionally as those for oral or parenteral administration. In this case, remarkably good effects can be obtained by using a compound exhibiting a 50% inhibitory concentration of cAMP production (IC50) of 100 nM or less. Moreover, for the purpose of allowing the same to act on the skin, they may be prepared in such dosage form that they may be directly administered on the skin by, e.g., application. In this case, they are prepared by incorporating into a cosmetic or an external preparation for the skin, at least one selected from the peptides of the present invention and salts thereof or a melanocyte-stimulating hormone inhibiting compound exhibiting a 50% inhibitory concentration of cAMP production (IC50) of 100 nM or less.

In these cases, at least one selected from the peptides and salts thereof of the present invention or a melanocyte-stimulating hormone inhibiting compound exhibiting a 50% inhibitory concentration of cAMP production (IC50) of 100 nM or less, may be incorporated into a cosmetic usually in an amount of 0.01 to 10% by weight, preferably 0.1 to 5% by weight, relative to the total amount of the cosmetic, and into an external preparation of the present invention usually in an amount of 0.01 to 50% by weight, preferably 0.1 to 20% by weight. When the amount is less than 0.01% by weight, the effect caused by the addition is not exhibited and therefore, such amount is not preferable. Whereas, when the amount is more than 50% by weight, there may be problems of feeling upon the use such as occurrence of creaky feeling toward the skin and therefore, such amount is not preferable either.

When at least one selected from the peptides and salts thereof of the present invention or a melanocyte-stimulating hormone inhibiting compound exhibiting a 50% inhibitory concentration of cAMP production (IC50) of 100 nM or less is used by incorporating the same into a cosmetic or an external preparation, ingredients generally used in cosmetics or external preparations may be added within the amount range where the effects intended by the present invention are not inhibited.

As examples of ingredients generally used in cosmetics or external preparations, there may be mentioned oily materials, surfactants, solvents, moisture keeping agents, polymeric substances, powdery substances, pigments, perfumes, other conventional ingredients, and the like.

The oily materials include oils and fats such as animal and vegetable oils, and the like, waxes such as lanolin, and the like, hydrocarbons such as paraffin, and the like, higher alcohols such as cetanol, and the like, higher fatty acids such as stearic acid, and the like, sterols, phospholipids such as lecithin, and the like, synthetic esters of myristic acid, and the like, metal soaps, silicone oils, and the like.

The surfactants include anionic surfactants, cationic surfactants, amphoteric surfactants, nonionic surfactants, emulsifying or solubilizing agents, and the like.

The solvents include lower alcohols such as ethanol, and the like, ethers, glycerols, liquid nonionic surfactants, liquid oily materials, other organic solvents, water, and the like.

The moisture keeping agents include polyhydric alcohols such as glycerol, and the like, salts of organic acids such as pyrrolidonecarboxylic acid, and the like, urea, mucopolysaccharides such as hyaluronic acid, and the like, salts of amino acids such as proline, and the like, and the like.

The polymeric substances include natural polymeric compounds such as collagen, and the like, semi-synthetic polymeric compounds such as partially deacetylated chitin, and the like, synthetic polymeric compounds such as carboxymethyl cellulose, and the like, and the like.

The powdery substances include inorganic pigments such as talc, and the like, functional pigments such as synthetic mica, and the like, hybrid fine powder, pearl-glossy pigments such as titanium dioxide-covered mica, and the like, photochromic pigments, polymeric powders such as nylon powder, and the like, organic powders such as $N^{\epsilon}$-lauroyllysine, and the like, and the like.

The pigments include the first class of the Japanese statutory tar pigments, the second class of the Japanese statutory tar pigments, the third class of the Japanese statutory tar pigments, hair dyes, natural pigments, mineral pigments, and the like.

The perfumes include animal perfumes such as musk, and the like, vegetable perfumes such as jasmine, and the like, synthetic perfumes such as α-amylcinnamaldehyde, and the like, blended perfumes, and the like.

The other conventional ingredients for cosmetics or external preparations for the skin include antiseptics/disinfectants, antioxidants, UV absorbers, chelating agents, antifading agents, buffering agents, medicines for acne, antiscurf and antiitch agents, antiperspirant deodorant, medicines for burns, acaricides/pediculicides, keratin softeners, medicines for xeroderma, antivirus agents, transdermal absorption promoting agents, hormones, vitamins, amino acids/peptides, proteins, astringents, anti-inflammatory agents, refrigerants/irritants, ingredients derived from animals or vegetables, melanin synthesis inhibitors (whitening agents), antibiotics, antifungal agents, hair growth agents, and the like.

The melanocyte-stimulating hormone inhibitory composition, whitening agent, immunofunction controlling agent, appetite controlling agent, cosmetic and external preparation for the skin of the present invention are not particularly limited in their dosage form, and they may take suitable dosage forms such as solutions, pastes, gels, solids, granules, powders, capsules, aerosols, and the like. More specifically, they may be used in the dosage form of oils, lotions, creams, emulsions, gels, shampoos, hair rinses, hair conditioners, enamels, foundations, lipsticks, face powders, packs, ointments, tablets, injections, granules, capsules, perfumes, powders, eau de Colognes, tooth pastes, soaps, aerosols, cleansing foams, and the like.

The melanocyte-stimulating hormone inhibitory composition, whitening agent, immunofunction controlling agent, appetite controlling agent, cosmetic and external preparation for the skin of the present invention can be used as agents for preventing or improving skin ageing, agents for preventing or improving skin inflammation, bath agents, hair growth agents, skin care solutions, anti-sunburn agents, agents for preventing or improving hyperesthesia optica such as xeroderma pigmentosum, solar urticaria, and the like, agents for preventing or improving photoallergy, agents for preventing or improving photoimmunosuppression, or agents for preventing or improving skin roughness due to trauma, chaps and cracks, and the like.

Furthermore, the melanocyte-stimulating hormone inhibitory composition or whitening agent of the present invention is useful for preventing or improving pigmentation by ultraviolet rays, and for preventing or improving chloasma, ephelides and senile pigment freckle.

Moreover, the melanocyte-stimulating hormone inhibitory composition of the present invention can be used as agents for preventing or treating various diseases in which melanocyte-stimulating hormone participates, such as immune abnormality or immunodeficiency, or for the purpose of the regulation of body weight by appetite control.

BEST MODE FOR CARRYING OUT THE INVENTION

Figure 1:
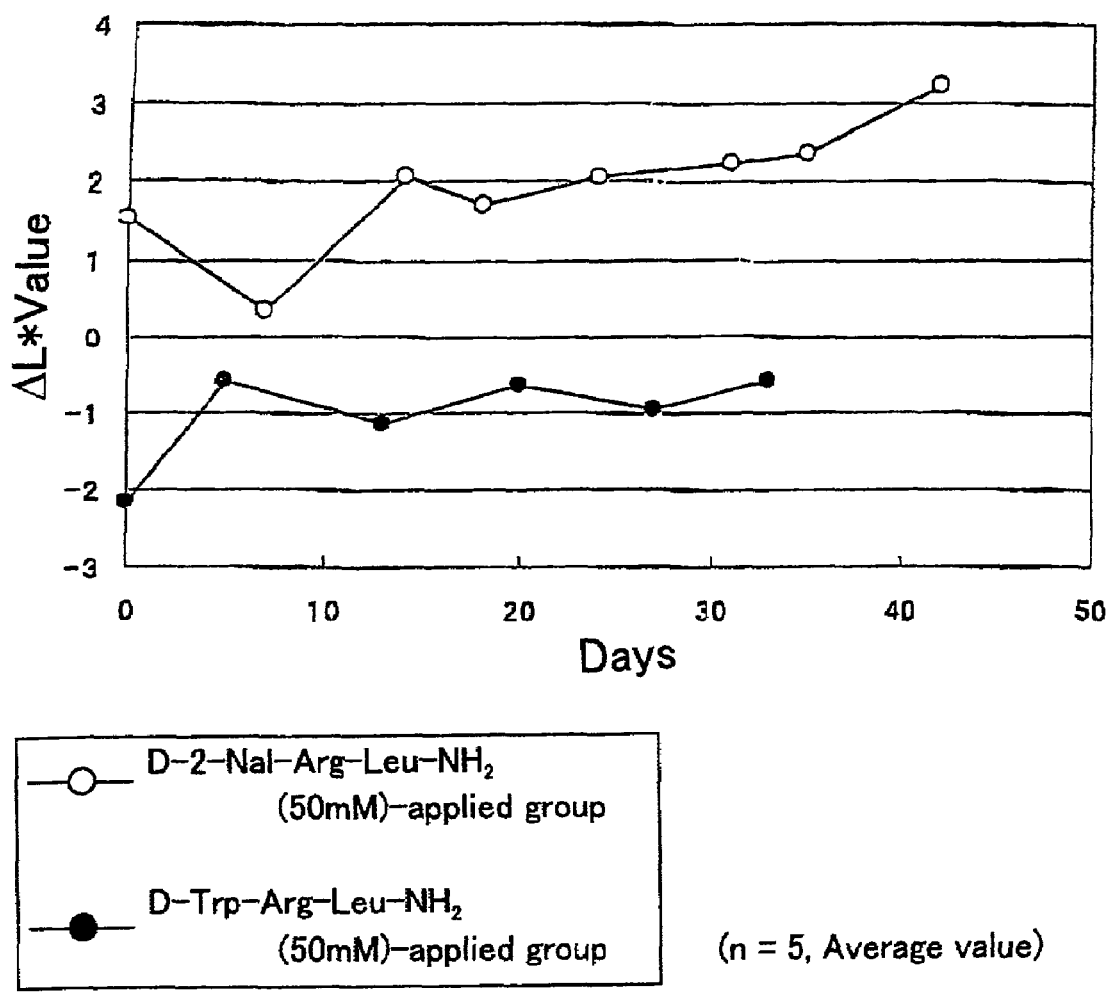
FIG. 1 shows the results of the inhibitory test on melanocyte-stimulating hormone in a living body (Test Example 4).

In the following will be described the present invention more specifically with reference to the examples, but the present invention is not limited these examples.

By the way, in the following examples, the incorporated amounts are represented in terms of % by weight, and naphthylalanyl group or naphthylalanine is abbreviated as Nal.

SYNTHETIC EXAMPLE 1

D-1-Nal-Arg-LeuNH$_2$

Boc-Arg (Z$_2$) (5 g, 9.22 mmol) was dissolved in methylene chloride (75 ml), and under ice-cooling, water-soluble carbodiimide hydrochloride (1.77 g, 9.22 mmol) and HOBt (1-hydroxybenzotriazole, 1.25 g, 9.22 mmol) were added thereto. Then, a methylene chloride solution (75 ml) of LeuNH$_2$ hydrochloride (1.61 g, 9.68 mmol) and triethylamine (1.91 g, 18.9 mmol) was added dropwise thereto over a period of 10 minutes, and the mixture was heated back to room temperature, followed by stirring overnight. The reaction liquid was concentrated under reduced pressure and then, ethyl acetate was added to the residue. The mixture was washed with 5% citric acid, 5% sodium hydrogen carbonate, and saturated saline, successively. After drying over magnesium sulfate, drying under reduced pressure afforded Boc-Arg (Z$_2$)-LeuNH$_2$ (5.8 g, 8.86 mmol).

A portion of the resulting Boc-Arg (Z$_2$)-LeuNH$_2$ (2 g, 3.1 mmol) was treated with trifluoroacetic acid (10 ml), whereby Arg(Z$_2$)-LeuNH$_2$ (1.28 g, 2.3 mmol) was obtained. Then, the resulting Arg(Z$_2$)-LeuNH$_2$ (1.28 g, 2.3 mmol) and Z-D-1-Nal (0.803 g, 2.3 mmol) were similarly condensed, whereby Z-D-1-Nal-Arg(Z$_2$)-LeuNH$_2$ (1.63 g, 1.84 mmol) was obtained. Next, the resulting Z-D-1-Nal-Arg(Z$_2$)-LeuNH$_2$ (1.63 g, 1.84 mmol) was dissolved in methanol (1,000 ml) and reduced in the presence of palladium-carbon catalyst, whereby D-1-Nal-Arg-LeuNH$_2$ (0.80 g, 1.66 mmol) was obtained.

SYNTHESIS EXAMPLE 2

D-2-Nal-Arg-LeuNH$_2$

Synthesis Example 1 was repeated except that Z-D-2-Nal was used instead of Z-D-1-Nal, whereby D-2-Nal-Arg-LeuNH$_2$ was obtained.

SYNTHESIS EXAMPLE 3

L-1-Nal-Arg-LeuNH$_2$

Synthesis Example 1 was repeated except that Z-L-1-Nal was used instead of Z-D-1-Nal, whereby L-1-Nal-Arg-LeuNH$_2$ was obtained.

SYNTHESIS EXAMPLE 4

L-2-Nal-Arg-LeuNH$_2$

Synthesis Example 1 was repeated except that Z-L-2-Nal was used instead of Z-D-1-Nal, whereby L-2-Nal-Arg-LeuNH$_2$ was obtained.

The results by the mass spectrometry (ESI-MS) of the compounds obtained by the above Synthesis Examples will be shown in the following Table 1.

TABLE 1

| Synthesis Example | Compounds | ESI mass spectra Molecular weight Calcd. | Found (MH+) |
|---|---|---|---|
| 1 | D-1-Nal-Arg-LeuNH$_2$ | 483 | 484 |
| 2 | D-2-Nal-Arg-LeuNH$_2$ | 483 | 484 |
| 3 | L-1-Nal-Arg-LeuNH$_2$ | 483 | 484 |
| 4 | L-2-Nal-Arg-LeuNH$_2$ | 483 | 484 |

TEST EXAMPLE 1

Measurement of 50% Inhibitory Concentration of cAMP Production (IC50)

According to the method of measuring the 50% inhibitory concentration of cAMP production (IC50) explained in the above, IC50 was measured on the agents listed in following Table 2, i.e., D-1-Nal-Arg-LeuNH$_2$, D-2-Nal-Arg-LeuNH$_2$, L-1-Nal-Arg-LeuNH$_2$ and D-Trp-Arg-LeuNH$_2$.

Results will be shown in Table 2. As shown in the table, the agents tested inhibited effectively the cAMP increasing action by melanocyte-stimulating hormone.

TABLE 2

Test on inhibition against melanocyte-stimulating hormone

| Test Compound | 50% inhibitory concentration (IC50, nM) |
|---|---|
| D-1-Nal-Arg-LeuNH$_2$ | 540 |
| D-2-Nal-Arg-LeuNH$_2$ | 42 |
| L-1-Nal-Arg-LeuNH$_2$ | 470 |
| D-Trp-Arg-LeuNH$_2$ | 230 |

TEST EXAMPLE 2

Test on Suppression of the Melanin Formation Caused by Human Melanocytes

Human melanocytes in logarithmic growth phase were treated with trypsin and inoculated to a 6-well plate with "Medium 154s" (manufactured by Kurabo Industries Ltd., containing a growth factor (HMGS)), in an amount of $1.5 \times 10^5$ per 1 well in terms of cell number. The cells were cultured at 37° C. in a carbon dioxide incubator, the $CO_2$ concentration being 5%, for 1 day. Thereafter, rinsing was carried out with the use of HBS (Hepes Buffer Saline), followed by medium replacement with "MCDB153" (containing fetal bovine serum, insulin, b-FGF, transferrin, and tocopherol), and followed by culturing for further 2 days. A whitening agent (containing a compound to be tested) was prepared with "MCDB153" (containing fetal bovine serum, insulin, b-FGF, transferrin, and tocopherol)+melanocyte-stimulating hormone in such way that the concentration would be 200 µM, 20 µM, or 2 µM, and was added to the 6-well plate. Also, a further 6-well plate culture was carried out with the use of "MCDB153" (containing fetal bovine serum, insulin, b-FGF, transferrin, and tocopherol)+melanocyte-stimulating hormone without the whitening agent, and still further a 6-well plate culture was carried out with the use of "MCDB153" (containing fetal bovine serum, insulin, b-FGF, transferrin, and tocopherol) alone, at the same time. The medium replacement with the above "MCDB153" (containing fetal bovine serum) containing a whitening agent was carried out twice every 2 days.

After the first addition of the whitening agent, the effect of suppressing the melanin formation was confirmed on the 6th day. Namely, the medium on each 6-well plate was removed by suction, and the wells were rinsed with HBS. Thereafter, the 6-well plate was air-dried, and ⅕M NaOH (230 µl) was added to the wells to dissolve the melanin out of the melanocytes. The solution (200 µl) was evaluated by Abs (absorbance) on a microplate reader (475 nm). The suppression rate of the melanin formation by each compound tested was calculated according to the following equation (1). The results will be shown below in Table 3.

$$\text{The suppression rate of the melanin formation}(\%) = \{1-(A_1-A_3)/(A_2-A_3)\} \times 100 \quad (1)$$

$A_1$: absorbance at 475 nm when both of the compound to be tested and MSH were added.

$A_2$: absorbance at 475 nm when the compound to be tested was not added and MSH was added.

$A_3$: absorbance at 475 nm when both of the compound to be tested and MSH were not added.

TABLE 3

Test on suppression of the melanin formation

| Compounds tested | Concentration (µM) | Suppression rate (%) |
|---|---|---|
| D-1-Nal-Arg-LeuNH$_2$ | 20 | 43 |
|  | 200 | 52 |
| D-2-Nal-Arg-LeuNH$_2$ | 2 | 49 |
|  | 20 | 51 |
|  | 200 | 70 |
| L-1-Nal-Arg-LeuNH$_2$ | 20 | 8 |
|  | 200 | 28 |
| D-Trp-Arg-LeuNH$_2$ | 20 | 24 |
|  | 200 | 57 |

As is shown in Table 3, the test compounds suppressed effectively the melanin formation by the melanocytes, increased by the addition of the melanocyte-stimulating hormone. It can be understood from this that the test compounds have an inhibitory activity of the melanin formation induced by melanocyte stimulating hormone.

TEST EXAMPLE 3

Test of Stability During Storage

An aqueous 0.1% solution of D-2-Nal-Arg-LeuNH$_2$ of the present invention, and that of D-Trp-Arg-LeuNH$_2$ which is a known melanocyte-stimulating hormone inhibitor were prepared and stored at 4° C. for 6 months, respectively. The stability during storage was evaluated by comparing the degree of coloring with standard colors of APHA (American Public Healthy Association) method. The results will be shown in the following Table 4.

TABLE 4

Test of stability during storage

| Compounds tested | | Degree of coloring (APHA Standard color) |
|---|---|---|
| Example | D-2-Nal-Arg-LeuNH$_2$ | 20 |
| Comparative Example | D-Trp-Arg-LeuNH$_2$ | 200 |

As is shown in Table 4, D-2-Nal-Arg-LeuNH$_2$ of the present invention showed an APHA value of 20 and was almost not colored, whereas D-Trp-Arg-LeuNH$_2$, a known melanocyte-stimulating hormone inhivitor showed an APHA value of 200 and was much colored. It can be understood from this, that D-2-Nal-Arg-LeuNH$_2$ of the present invention has a good stability.

TEST EXAMPLE 4

Inhibitory Test of Melanocyte-Stimulating Hormone in Living Body (Test of Suppressing Pigmentation in Brown Guinea Pigs)

Inhibitory test of melanocyte-stimulating hormone was carried out by repeating the application of each test compound on a guinea pig and irradiation with ultraviolet rays, followed by measuring the degree of coloring, as follows.

1. Compounds to be Tested:

D-2-Nal-Arg-LeuNH$_2$ (50 mM, dissolved in 50% ethanol-water) and D-Trp-Arg-LeuNH$_2$ (50 mM, dissolved in 50% ethanol-water) were used, and 50% ethanol-water was used as the control.

2. Animal for Evaluation:

Male Weiser-Maples brown guinea pigs (4 weeks old) were purchased from Tokyo Experimental Animal K.K. and used after pre-reared for 7 weeks.

3. Shaving of the Brown Guinea Pigs:

The brown guinea pigs were individually fixed by means of a fixing instrument and shaved in a square shape of about 3 cm×3 cm on their back with the use of a pair of hair clippers "THRIVE MODEL 6000AD" (manufactured by Natsume Seisakusyo) and "Home Hair Clipper Ceramic ER722" (manufactured by National) and an electric shaver "Dual 1500AC/RC" (manufactured by BRAUN). The skin after shaved was wiped with a water-soaked absorbent cotton, and the moisture was removed with a paper towel "KIMWIPE" (manufactured by CRECIA).

4. Tape Stripping:

The exfoliation of part of the horny layer by detaching an adhesive tape which has been attached onto the skin surface is herein referred to as "tape stripping".

The skin of the back of the shaven brown guinea pigs was wiped with an ethanol-soaked absorbent cotton, and the horny layer having an area of about 2 cm×2 cm was subjected to tape stripping five times with the use of an adhesive tape "Scotch 313D" (manufactured by 3M).

By the way, tape stripping was similarly carried out after one month.

5. Application of the Compound to be Tested:

From the next day of the day when the tape stripping had been carried out, a sample was applied onto the part for evaluation of the skin at the frequency given below. The application was carried out by means of "PIPETMAN" (manufactured by GILSON) so as to spread the compound to be tested or the control one for comparison.

(1) Before the Term of the Irradiation with Ultraviolet Rays (the Term Between the Finish of the Tape Stripping and the Start, I.E., 5 Days after, of Irradiation with Ultraviolet Rays):

The sample was applied once a day in an amount of 10 μl onto the predetermined part (for 5 days).

(2) During the Term of Irradiation with Ultraviolet Rays:

After every irradiation with ultraviolet rays, the sample was applied onto the predetermined part. The application of the sample was carried out twice a day (in the morning and in the evening), in an amount of 10 μl for 5 days per 1 week (from Monday to Friday) (for 2 weeks).

(3) After the Term of the Irradiation with Ultraviolet Rays:

The sample was applied twice a day (in the morning and in the evening) in an amount of 10 μl for 5 days per 1 week (from Monday to Friday) (for 40 days).

By the way, in order to cancel the effect of absorption of ultraviolet rays by a sample during the term of the irradiation with ultraviolet rays, upon the application of the sample, the test compound of D-2-Nal-Arg-LeuNH$_2$ (or D-Trp-Arg-LeuNH$_2$) was also applied even to the 50% ethanol-applied group. From the time when the irradiation with ultraviolet rays had been terminated, 50% ethanol was applied to the 50% ethanol-applied group.

6. Irradiation with Ultraviolet Rays:

The irradiation with ultraviolet rays was carried out once a day on three days a week (Monday, Wednesday, and Friday), i.e., 6 times in total after the passage of 5 days from the day when the tape stripping had been conducted.

Immediately before the irradiation with ultraviolet rays, the brown guinea pigs were shaven on the back in a similar manner to the above, every time, and the part for evaluation was washed with water to remove the compound to be tested, and then an excess water was removed with a paper towel. The brown guinea pigs were individually fixed by means of a fixing instrument and irradiated with UVB with the eyes being protected with an aluminum foil (Apparatus for irradiation with ultraviolet rays "Dermaray M-DMR-80 type" (Clinical Supply)). The irradiation was carried out under the conditions of 0.5 mW×5 minutes and the intensity of ultraviolet rays was controlled by measuring by means of a ultraviolet rays meter "UVR-305/365-D (II)" (Clinical Supply).

7. Evaluation:

Evaluation was conducted by measuring L* on a spectrocolorimeter "CM-2002" (manufactured by Minolta) once or twice a week. Incidentally, the L* value is one of the numerical values of L*a*b* color system and represents brightness. The L*a*b* color system is standardized by the International Commission on Illumination (CIE) in 1976, and also adopted in JIS (Japanese Industrial Standard) in Japan (JIS Z8729).

By the way, immediately before the evaluation, the brown guinea pigs were shaven on the back in a similar manner to the above, every time, and the part for evaluation was washed with water to remove the compound to be tested, and then an excess water was removed with a paper towel.

The results will be shown later in FIG. 1. In FIG. 1, the vertical axis represents the difference between the L* value at the evaluated part onto which D-2-Nal-Arg-LeuNH$_2$ (or D-Trp-Arg-LeuNH$_2$) was applied and the L* value at the evaluated part onto which 50% ethanol was applied, as ΔL* value. The horizontal axis represents day(s). The 0th day from the start of the evaluation means the day when the irradiation with ultraviolet rays was finished. The larger the ΔL* value is, the smaller the pigmentation is, and this means inhibition of melanocyte-stimulating hormone.

From these results, it can be understood that the compounds having a melanocyte-stimulating hormone inhibitory activity, i.e., a 50% inhibitory concentration of cAMP production (IC50) of 100 nM or less, exhibit a sufficient inhibitory effect against melanocyte-stimulating hormone in a living body.

The above test results will be summarized in the following Table 5.

TABLE 5

Evaluation results of MSH inhibitors

| Test compounds | MSH inhibitory activity | Melanin formation suppressing activity | Stability during storage | Brown Guinea pig pigmentation suppressing test |
|---|---|---|---|---|
| D-1-Nal-Arg-LeuNH$_2$ | B | B | — | — |
| D-2-Nal-Arg-LeuNH$_2$ | A | A | A | ◯ |
| L-1-Nal-Arg-LeuNH$_2$ | B | B | — | — |
| D-Trp-Arg-LeuNH$_2$ | B | B | C | X |

The standards of the evaluations in Table 5 are as follows:

(1) MSH Inhibitory Activity:

| 50% Inhibitory concentration in the test | Evaluation |
|---|---|
| 100 nM or less | A |
| 101 to 1000 nM | B |
| 1001 nM or more | C |

(2) Melanin Formation Suppressing Activity:

| Minimum concentration showing melanin formation suppressing activity in the test | Evaluation |
|---|---|
| 1 to 10 μM | A |
| 11 to 100 μM | B |
| 101 μM or more | C |

(3) Test on Stability During Storage:

| Degree of coloring in the test (APHA standard colors) | Evaluation |
|---|---|
| 20 or less | A |
| 21 to 100 | B |
| 101 or more | C |
| not tested | — |

(4) Brown Guinea Pig Pigmentation Suppressing Test:

| | Evaluation |
|---|---|
| positive pigmentation suppressing effect | ◯ |
| no pigmentation suppressing effect | X |
| not tested | — |

From the above table, it can be understood that the compounds of the present invention are advantageous as a whole.

Melanocyte-stimulating hormone inhibitory compositions, cosmetics or skin preparations for external use were prepared in an ordinary way in accordance with the compositions indicated in the following Formulation Examples 1-11.

| | wt % |
|---|---|
| Formulation Example 1: Tablet | |
| D-2-Nal-Arg-LeuNH$_2$ | 10 |
| Milk sugar | 50 |
| Starch | 20 |
| Carboxymethyl cellulose | 19 |
| Magnesium stearate | 1 |
| Formulation Example 2: Injection | |
| D-2-Nal-Arg-LeuNH$_2$ | 0.1 |
| Grape sugar | 2.0 |
| Injection water | balance |
| Formulation Example 3: Ointment | |
| N-Lauroyl-D-2-Nal-Arg-LeuNH$_2$ | 1.0 |
| Urea | 20.0 |
| White vaseline | 15.0 |
| Light liquid paraffin | 6.0 |
| Cetanol | 3.0 |
| Stearyl alcohol | 5.0 |
| Glycerol monostearate | 5.0 |
| Perfume | proper amount |
| Preservative | proper amount |
| Buffer | 1 |
| Purified water | balance |
| Formulation Example 4: Cream | |
| D-2-Nal-Arg-LeuOEt | 1.0 |
| Kojic acid | 1.0 |
| Stearic acid | 2.0 |
| Poly(oxyethylene) (25)cetyl ether | 3.0 |
| Glycerol monostearate | 2.0 |
| Octyl dodecanol | 10.0 |
| Cetanol | 6.0 |
| Reduced lanolin | 4.0 |
| Squalane | 9.0 |
| 1,3-Butylene glycol | 6.0 |
| Polyethylene glycol (1500) | 4.0 |
| Preservative | proper amount |
| Perfume | proper amount |
| Purified water | balance |

| | wt % |
|---|---|
| Formulation Example 5: Cream | |
| D-2-Nal-Arg-LeuOEt | 1.0 |
| Arbutin | 1.0 |
| Stearic acid | 2.0 |
| Poly(oxyethylene) (25)cetyl ether | 3.0 |
| Glycerol monostearate | 2.0 |
| Octyl dodecanol | 10.0 |
| Cetanol | 6.0 |
| Reduced lanolin | 4.0 |
| Squalane | 9.0 |
| 1,3-Butylene glycol | 6.0 |
| Polyethylene glycol (1500) | 4.0 |
| Preservative | proper amount |
| Perfume | proper amount |
| Purified water | balance |
| Formulation Example 6: Milky lotion | |
| D-1-Nal-Arg-LeuNH$_2$ | 2.0 |
| Retinol | 0.1 |
| Beeswax | 0.5 |
| Vaseline | 2.0 |
| Glycerol monostearate | 1.0 |
| Polyethylene glycol monooleate | 1.0 |
| Methylpolysiloxane | 2.0 |
| Cetanol | 1.0 |
| Squalane | 6.0 |
| Carboxyvinyl polymer | 0.5 |
| 1,3-Butylene glycol | 4.0 |
| Ethanol | 5.0 |
| Preservative | proper amount |
| Perfume | proper amount |
| Purified water | balance |
| Formulation Example 7: Gel | |
| N-Acetyl-D-1-Nal-Arg-LeuNH$_2$ | 0.1 |
| Liquid paraffin | 12.0 |
| Glycerol tri(2-ethylhexanoate) | 50.0 |
| Sorbit | 10.0 |
| Polyethylene glycol (400) | 5.0 |
| Acylmethyltaurine | 5.0 |
| Poly(oxyethylene) (20)isocetyl ether | 10.0 |
| Preservative | proper amount |
| Perfume | proper amount |
| Purified water | balance |
| Formulation Example 8: Cosmetic liquid | |
| D-2-Nal-Arg-LeuNH$_2$ | 0.5 |
| Dipropylene glycol | 5.0 |
| Polyethylene glycol (400) | 5.0 |
| Ethanol | 10.0 |
| Carboxyvinyl polymer | 0.5 |
| Sodium alginate | 0.5 |
| Potassium hydroxide | 0.2 |
| Poly (oxyethylene) (20)sorbitan monostearate | 1.0 |
| Sorbit monooleate | 0.5 |
| Oleyl alcohol | 0.5 |
| Placenta extract | 0.2 |
| dl-α-tocophenol acetate | 0.2 |
| Preservative | proper amount |
| Perfume | proper amount |
| Anti-fading agent | proper amount |
| Purified water | balance |
| Formulation Example 9: Pack | |
| L-1-Nal-Arg-LeuNH$_2$ | 3.0 |
| Poly (vinyl alcohol) | 15.0 |
| Carboxymethyl cellulose | 5.0 |
| 1, 3-Butylene glycol | 5.0 |
| Ethanol | 12.0 |
| Poly(oxyethylene) (20)oleyl ether | 0.5 |
| Preservative | proper amount |
| Perfume | proper amount |
| Buffer | proper amount |
| Purified water | balance |

| | wt % |
|---|---|
| Formulation Example 10: Foundation | |
| N-Lauroyl-L-1-Nal-Arg-LeuNH$_2$ | 5.0 |
| Liquid paraffin | 10.0 |
| Poly(oxyethylene) (20)sorbitan monostearate | 3.5 |
| Propylene glycol | 3.0 |
| Titanium oxide | 9.0 |
| Kaolin | 24.0 |
| Talc | 42.0 |
| Coloring pigment | 3.0 |
| Preservative | proper amount |
| Per fume | proper amount |
| Purified water | balance |
| Formulation Example 11: Face wash | |
| L-1-Nal-Arg-LeuNH$_2$ | 0.5 |
| Triethanolamine N-lauroylglutamate | 25.0 |
| Triethanolamine laurate | 5.0 |
| Poly(oxyethylene) (4)poly(oxypropylene) (11)butyl ether | 5.0 |
| Ethanol | 3.0 |
| Preservative | proper amount |
| Perfume | proper amount |
| Purified water | balance |

INDUSTRIAL APPLICABILITY

The peptide derivatives and melanocyte-stimulating hormone inhibitory compositions of the present invention can inhibit the action of melanocyte-stimulating hormone, whereby pigmentation can be prevented, can prevent, improve or recover from immune abnormality or immunodeficiency, or regulate body weight by appetite control, and also can be used as cosmetics or external preparations for the skin, and in addition, can be produced easily, and are excellent in the stability during storage.

The invention claimed is:

1. A compound represented by the following Formula (1) or a salt thereof

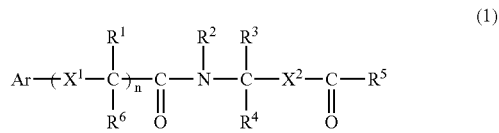

wherein $R^5$ represents a group represented by the following Formula (2),

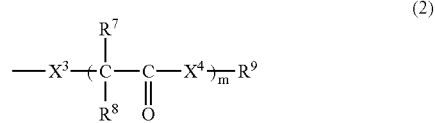

wherein m is 1 and:
Ar represents an unsubstituted naphthyl group,
$R^1$, $R^2$ and $R^3$ each represent independently a hydrogen atom, an unsubstituted straight-chain alkyl group having 1 to 6 carbon atoms, an unsubstituted branched-chain alkyl group having 1 to 6 carbon atoms, R⁴ represents an unsubstituted basic amino acid side chain, X¹ is an unsubstituted alkylene group having 1 to 6 carbon atoms, X² is a single bond, R⁶ represents a hydrogen atom or —NHY, wherein Y represents a hydrogen atom, an acyl group having 2 to 22 carbon atoms, an alkyl group having 1 to 22 carbon atoms, a hydroxyalkyl group having 1 to 22 carbon atoms, or a 3-alkoxy-2-hydroxypropyl group wherein the alkoxyl group has 1 to 22 carbon atoms, n is 1, X³ represents —NR¹⁰—, X⁴ represents —O— or —NR¹¹—, R⁷ represents a side chain of an amino acid having a hydrophobic side chain selected from the group consisting of valine, norvaline, leucine, norleucine, isoleucine, phenylalanine, phenylglycine, threonine, and tryptophan, R⁸, R¹⁰, and R¹¹ each represent independently a hydrogen atom or a straight-chain or branched-chain alkyl group having 1 to 6 carbon atoms, R⁹ represents a hydrogen atom, an acyl group having 2 to 22 carbon atoms, or an alkyl group having 1 to 22 carbon atoms.

2. The compound or salt thereof as claimed in claim 1, wherein said compound represented by Formula (1) is D-1-naphthylalanyl-Arg-LeuNH₂, D-2-naphthylalanyl-Arg-LeuNH₂, L-1-naphthylalanyl-Arg-LeuNH₂ or L-2-naphthylalanyl-Arg-LeuNH₂.

3. The compound or salt thereof as claimed in claim 2, wherein said compound represented by Formula (1) is D-1-naphthylalanyl-Arg-LeuNH₂.

4. The compound or salt thereof as claimed in claim 2, wherein said compound represented by Formula (1) is D-2-naphthylalanyl-Arg-LeuNH₂.

5. The compound or salt thereof as claimed in claim 2, wherein said compound represented by Formula (1) is L-1-naphthylalanyl-Arg-LeuNH₂.

6. The compound or salt thereof as claimed in claim 2, wherein said compound represented by Formula (1) is L-2-naphthylalanyl-Arg-LeuNH₂.

7. The compound or salt thereof as claimed in claim 1, wherein

Ar of Formula (1) represents a 1-naphthyl group or a 2-naphthyl group,

R¹, R² and R³ of Formula (1) each represent a hydrogen atom,

R⁴ of Formula (1) represents an unsubstituted basic amino acid side chain having an amino group or a guanidino group, X¹ of Formula (1) is a methylene group, R⁶ of Formula (1) represents —NHY, wherein Y represents a hydrogen atom, an acyl group having 2 to 22 carbon atoms, an alkyl group having 1 to 22 carbon atoms, a hydroxyalkyl group having 1 to 22 carbon atoms, or a 3-alkoxy-2-hydroxypropyl group wherein the alkoxyl group has 1 to 22 carbon atoms, wherein X³ of Formula (2) represents —NH—, X⁴ of Formula (2) represents —O— or —NH—, R⁷ of formula (2) represents a side chain of a neutral amino acid having a hydrophobic side chain selected from the group consisting of valine, norvaline, leucine, norleucine, isoleucine, phenylalanine, phenylglycine, and threonine, R⁸ of Formula (2) represents a hydrogen atom, R⁹ of Formula (2) represents a hydrogen atom, an acyl group having 2 to 22 carbon atoms, or an alkyl group having 1 to 22 carbon atoms.

8. A melanocyte-stimulating hormone inhibitory composition which comprises, as an active ingredient, at least one compound or salt thereof as claimed in claim 1, and a cosmetically acceptable carrier.

9. A whitening agent which comprises, as an active ingredient, at least one compound or salt thereof of the composition as claimed in claim 8 and a cosmetically acceptable carrier, wherein said whitening agent is an inhibitor of pigmentation by ultraviolet rays.

10. A cosmetic or external preparation for the skin which comprises, as an active ingredient, at least one compound or salt thereof as claimed in claim 8 and a cosmetically acceptable carrier.

11. A method of whitening which comprises, contacting an object to be whitened with an effective amount of a whitening agent comprising as an active ingredient, at least one compound or salt thereof of the composition as claimed in claim 8, wherein said whitening agent is an inhibitor of pigmentation by ultraviolet rays.

12. A melanocyte-stimulating hormone inhibitory composition which comprises, as an active ingredient, a compound or salt thereof as claimed in claim 1 that exhibits a 50% inhibitory concentration of cAMP production (IC50) of 100 nM or less, and a cosmetically acceptable carrier.

13. The melanocyte-stimulating hormone inhibitory composition as claimed in claim 12, wherein said composition is an inhibitor of pigmentation by ultraviolet rays.

14. The melanocyte-stimulating hormone inhibitory composition as claimed in claim 12, wherein said melanocyte-stimulating hormone inhibitory compound has a molecular weight of 800 or less.

15. A cosmetic or external preparation for the skin which comprises, as an active ingredient, at least one compound or salt thereof as claimed in claim 12 and a cosmetically acceptable carrier.

16. A method of whitening which comprises, contacting an object to be whitened with an effective amount of a whitening agent comprising as an active ingredient, at least one compound or salt thereof of the composition as claimed in claim 12, wherein said whitening agent is an inhibitor of pigmentation by ultraviolet rays.

17. A cosmetic or external preparation for the skin which comprises, as an active ingredient, at least one compound or salt thereof as claimed in claim 1 and a cosmetically acceptable carrier.

18. A method of whitening which comprises, contacting an object to be whitened with an effective amount of a whitening agent comprising as an active ingredient, at least one compound or salt thereof as claimed in claim 1, wherein said whitening agent is an inhibitor of pigmentation by ultraviolet rays.

* * * * *

UNITED STATES PATENT AND TRADEMARK OFFICE
CERTIFICATE OF CORRECTION

PATENT NO. : 7,375,085 B1
APPLICATION NO. : 09/926391
DATED : May 20, 2008
INVENTOR(S) : Eiji Shiojiri et al.

Page 1 of 1

It is certified that error appears in the above-identified patent and that said Letters Patent is hereby corrected as shown below:

Column 13, line 33, "melanocyte-stimulating hormone inhivitor showed"
should read -- melanocyte-stimulating hormone inhibitor showed --.

Column 14, line 63, "ultraviolet rays "Dermaray M-DMR-80"
should read -- ultraviolet rays "Dermalay M-DMR-80 --.

Signed and Sealed this

Seventeenth Day of March, 2009

JOHN DOLL
*Acting Director of the United States Patent and Trademark Office*